(12) United States Patent
Ma (10) Patent No.: US 10,918,739 B2
(45) Date of Patent: Feb. 16, 2021

(54) SDR5-FC FUSION PROTEIN MUTANT AND USE THEREOF

(71) Applicant: SUZHOU YONGXIN BIOLOGICAL SCIENCE AND TECHNOLOGY CO., LTD., Suzhou Industrial Park (CN)

(72) Inventor: Yuanfang Ma, Henan (CN)

(73) Assignee: Suzhou Yongxin Biological Science and Technology Co., Ltd, Jiangsu Province (CN)

(*) Notice: Subject to any disclaimer, the term of this patent is extended or adjusted under 35 U.S.C. 154(b) by 215 days.

(21) Appl. No.: 15/738,210

(22) PCT Filed: May 10, 2016

(86) PCT No.: PCT/CN2016/081552
§ 371 (c)(1),
(2) Date: Dec. 20, 2017

(87) PCT Pub. No.: WO2017/028558
PCT Pub. Date: Feb. 23, 2017

(65) Prior Publication Data
US 2018/0161450 A1 Jun. 14, 2018

(30) Foreign Application Priority Data
Aug. 19, 2015 (CN) .......................... 201510510981.9

(51) Int. Cl.
*C07K 16/46* (2006.01)
*C07K 14/715* (2006.01)
(Continued)

(52) U.S. Cl.
CPC ........ *A61K 48/005* (2013.01); *A61K 38/1774* (2013.01); *A61K 38/1793* (2013.01);
(Continued)

(58) Field of Classification Search
CPC .................................................. C07K 14/70578
See application file for complete search history.

(56) References Cited

U.S. PATENT DOCUMENTS

| 6,313,269 B1* | 11/2001 | Deen ................ C07K 14/70578 |
| | | 435/69.1 |
| 2008/0248046 A1* | 10/2008 | Ni ..................... C07K 14/70578 |
| | | 424/139.1 |
| 2009/0136503 A1* | 5/2009 | Yu ..................... C07K 16/2878 |
| | | 424/138.1 |

FOREIGN PATENT DOCUMENTS

| CN | 104710533 | 6/2015 |
| CN | 105061604 | 11/2015 |

OTHER PUBLICATIONS

Lünemann et al., Death ligand TRAIL induces no apoptosis but inhibits activation of human (auto)antigen-specific T cells, J. Immunol. 168:4881-4888, 2002.*

(Continued)

*Primary Examiner* — Claire Kaufman
(74) *Attorney, Agent, or Firm* — Nixon & Vanderhye, PC (57) ABSTRACT

The present disclosure discloses a human sDR5-Fc fusion protein in the preparation of adjuvant therapy for myocardial ischemia-reperfusion injury. The sDR5-Fc antibody fusion protein of the disclosure is prepared by connecting the 182 amino acids in DR5 extracellular domain with the human anti-Fc fragments. It has been tested that the sDR5-Fc antibody fusion protein of the disclosure can basically avoid Fc-mediated ADCC effect and can significantly reduce the area of myocardial infarction in rats of myocardial ischemia-reperfusion models.

8 Claims, 3 Drawing Sheets

Specification includes a Sequence Listing.

(51) Int. Cl.

| | |
|---|---|
| *C12N 15/62* | (2006.01) |
| *C12N 5/10* | (2006.01) |
| *A61K 48/00* | (2006.01) |
| *C07K 14/705* | (2006.01) |
| *A61K 38/17* | (2006.01) |
| *A61P 9/00* | (2006.01) |
| *A61K 39/395* | (2006.01) |
| *C07K 19/00* | (2006.01) |

(52) U.S. Cl.
CPC ............ *A61K 39/3955* (2013.01); *A61P 9/00* (2018.01); *C07K 14/70578* (2013.01); *C07K 19/00* (2013.01); *C07K 2319/30* (2013.01)

(56) References Cited

OTHER PUBLICATIONS

Truneh et al., Differential recognition by CD28 of its cognate counter receptors CD80 (B7.1) and B70 (B7.2): analysis by site directed mutagenesis, Mol. Immunol. 33(3):321-334, 1996.*

Walczak et al., TRAIL-R2: a novel apoptosis-mediating receptor for TRAIL,The EMBO J. 16(17):5386-5397, 1997.*

Piechocki et al., Induction of proapoptotic antibodies to triple-negative breast cancer by vaccination with TRAIL death receptor DR5 DNA, Int. J. Cancer, 131:2562-2572, 2012.*

Beck et al., Therapeutic Fc-fusion proteins and peptides as successful alternatives to antibodies, mAbs, 3(5):415-516, 2011.*

Exbio Praha,Technical Data Sheet, Recombinant human TRAIL-R2(DR5)/Fc Chimera Retrieved from <https://www.exbio.cz/getattachment/84183051-5052-4f8f-ad77-9f05490f25f3/EXB0007_TDS_-20190530-223135626.pdf.aspx> [Retrieved on Oct. 9, 2020]. <span style="font-family: "Windows Arial Unicode";"> revised May 3, 2019.</spa.*

Li, X, Protection of sDR5-Fc against ischemia-reperfusion injury of kidney in mice, Master's Dissertation, Henan University, Retreived from<http://cdmd.cnki.com.cn/Article/CDMD-10475-1016201591.htm> [Retrieved on Oct. 9, 2020] Jun. 1, 2016.*

R&D Systems, Product Datasheet, Recombinant human TRAIL R2/TNFRSF10B Fc chimera, Retrieved from <https://resources.rndsystems.com/pdfs/datasheets/10140-t2.pdf> [Retrieved on Oct. 9, 2020], revised Dec. 9, 2019.*

Smith et al.,CD30 antigen, a marker for Hodgkin's lymphoma, is a receptor whose ligand defines an emerging family of cytokines with homology to TNF, Cell, 73(7):1349-1360, '993.*

Fanslow et al., Soluble forms of CD40 inhibit biologic responses to human B cells, J. Immunol.149:655-660, 1992.*

International Search Report of PCT/CN2016/081552, dated Aug. 11, 2016, 3 pages.

Ma et al. "Protection of protein sDR5 for cardiomyocyte of acute myocardial infarction rat", Proceedings of the 9th Annual Meeting of Chinese Society for Immunology, Oct. 18, 2014, p. 590-591 (with English translation).

* cited by examiner

SEQUENCE LISTING

<160> NUMBER OF SEQ ID NOS: 11

<210> SEQ ID NO 1
<211> LENGTH: 182
<212> TYPE: PRT
<213> ORGANISM: Homo sapiens

<400> SEQUENCE: 1

Met Glu Gln Arg Gly Gln Asn Ala Pro Ala Ala Ser Gly Ala Arg Lys
1               5                   10                  15

Arg His Gly Pro Gly Pro Arg Glu Ala Arg Gly Ala Arg Pro Gly Pro
            20                  25                  30

```
Arg Val Pro Lys Thr Leu Val Val Val Ala Ala Val Leu Leu Leu
         35                  40                  45

Val Ser Ala Glu Ser Ala Leu Ile Thr Gln Gln Asp Leu Ala Pro Gln
 50                  55                  60

Gln Arg Ala Ala Pro Gln Gln Lys Arg Ser Ser Pro Ser Glu Gly Leu
 65                  70                  75                  80

Cys Pro Pro Gly His His Ile Ser Glu Asp Gly Arg Asp Cys Ile Ser
                 85                  90                  95

Cys Lys Tyr Gly Gln Asp Tyr Ser Thr His Trp Asn Asp Leu Leu Phe
                100                 105                 110

Cys Leu Arg Cys Thr Arg Cys Asp Ser Gly Glu Val Glu Leu Ser Pro
                115                 120                 125

Cys Thr Thr Thr Arg Asn Thr Val Cys Gln Cys Glu Glu Gly Thr Phe
                130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu
                180

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
                 35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
                115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
                195                 200                 205

Ser Cys Ser Val Met His Glu Ala Leu His Asn His Tyr Thr Gln Lys
```

```
                    210                 215                 220
Ser Leu Ser Leu Ser Pro Gly Lys
225                 230

<210> SEQ ID NO 3
<211> LENGTH: 414
<212> TYPE: PRT
<213> ORGANISM: Homo sapiens

<400> SEQUENCE: 3

Met Glu Gln Arg Gly Gln Asn Ala Pro Ala Ser Gly Ala Arg Lys
1               5                   10                  15

Arg His Gly Pro Gly Pro Arg Glu Ala Arg Gly Ala Arg Pro Gly Pro
                20                  25                  30

Arg Val Pro Lys Thr Leu Val Leu Val Val Ala Ala Val Leu Leu Leu
            35                  40                  45

Val Ser Ala Glu Ser Ala Leu Ile Thr Gln Gln Asp Leu Ala Pro Gln
50                  55                  60

Gln Arg Ala Ala Pro Gln Gln Lys Arg Ser Ser Pro Ser Glu Gly Leu
65                  70                  75                  80

Cys Pro Pro Gly His His Ile Ser Glu Asp Gly Arg Asp Cys Ile Ser
                85                  90                  95

Cys Lys Tyr Gly Gln Asp Tyr Ser Thr His Trp Asn Asp Leu Leu Phe
            100                 105                 110

Cys Leu Arg Cys Thr Arg Cys Asp Ser Gly Glu Val Glu Leu Ser Pro
        115                 120                 125

Cys Thr Thr Thr Arg Asn Thr Val Cys Gln Cys Glu Glu Gly Thr Phe
130                 135                 140

Arg Glu Glu Asp Ser Pro Glu Met Cys Arg Lys Cys Arg Thr Gly Cys
145                 150                 155                 160

Pro Arg Gly Met Val Lys Val Gly Asp Cys Thr Pro Trp Ser Asp Ile
                165                 170                 175

Glu Cys Val His Lys Glu Ser Gly Pro Lys Ser Cys Asp Lys Thr His Thr
            180                 185                 190

Cys Pro Pro Cys Pro Ala Pro Glu Leu Leu Gly Gly Pro Ser Val Phe
        195                 200                 205

Leu Phe Pro Pro Lys Pro Lys Asp Thr Leu Met Ile Ser Arg Thr Pro
210                 215                 220

Glu Val Thr Cys Val Val Val Asp Val Ser His Glu Asp Pro Glu Val
225                 230                 235                 240

Lys Phe Asn Trp Tyr Val Asp Gly Val Glu Val His Asn Ala Lys Thr
                245                 250                 255

Lys Pro Arg Glu Glu Gln Tyr Asn Ser Thr Tyr Arg Val Val Ser Val
            260                 265                 270

Leu Thr Val Leu His Gln Asp Trp Leu Asn Gly Lys Glu Tyr Lys Cys
        275                 280                 285

Lys Val Ser Asn Lys Ala Leu Pro Ala Pro Ile Glu Lys Thr Ile Ser
290                 295                 300

Lys Ala Lys Gly Gln Pro Arg Glu Pro Gln Val Tyr Thr Leu Pro Pro
305                 310                 315                 320

Ser Arg Asp Glu Leu Thr Lys Asn Gln Val Ser Leu Thr Cys Leu Val
                325                 330                 335

Lys Gly Phe Tyr Pro Ser Asp Ile Ala Val Glu Trp Glu Ser Asn Gly
            340                 345                 350
```

```
Gln Pro Glu Asn Asn Tyr Lys Thr Thr Pro Val Leu Asp Ser Asp
            355                 360                 365

Gly Ser Phe Phe Leu Tyr Ser Lys Leu Thr Val Asp Lys Ser Arg Trp
    370                 375                 380

Gln Gln Gly Asn Val Phe Ser Cys Ser Val Met His Glu Ala Leu His
385                 390                 395                 400

Asn His Tyr Thr Gln Lys Ser Leu Ser Leu Ser Pro Gly Lys
                405                 410
```

<210> SEQ ID NO 4
<211> LENGTH: 1245
<212> TYPE: DNA
<213> ORGANISM: Homo sapiens

<400> SEQUENCE: 4

```
atggaacaac ggggacagaa cgccccggcc gcttcggggg cccggaaaag gcacggccca      60
ggacccaggg aggcgcgggg agccaggcct gggccccggg tccccaagac ccttgtgctc     120
gttgtcgccg cggtcctgct gttggtctca gctgagtctg ctctgatcac caacaagac     180 ctagctcccc agcagagagc ggccccacaa caaaagaggt ccagcccctc agagggattg     240
tgtccacctg acaccatat ctcagaagac ggtagagatt gcatctcctg caaatatgga     300
caggactata gcactcactg gaatgacctc cttttctgct tgcgctgcac caggtgtgat     360
tcaggtgaag tggagctaag tccctgcacc acgaccagaa acacagtgtg tcagtgcgaa     420
gaaggcacct tccgggaaga agattctcct gagatgtgcc ggaagtgccg cacagggtgt     480
cccagaggga tggtcaaggt cggtgattgt acacctggga gtgacatcga atgtgtccac     540
aaagaagagc ccaaatcttg tgacaaaact cacacatgcc caccgtgccc agcacctgaa     600
ctcctggggg gaccgtcagt cttcctcttc cccccaaaac ccaaggacac cctcatgatc     660
tcccggaccc ctgaggtcac atgcgtggtg gtggacgtga gccacgaaga ccctgaggtc     720
aagttcaact ggtacgtgga cggcgtggag gtgcataatg ccaagacaaa gccgcgggag     780
gagcagtaca acagcacgta ccgtgtggtc agcgtcctca ccgtcctgca ccaggactgg     840
ctgaatggca aggagtacaa gtgcaaggtc tccaacaaag ccctcccagc ccccatcgag     900
aaaaccatct ccaaagccaa agggcagccc cgagaaccac aggtgtacac cctgccccca     960
tcccgggatg agctgaccaa gaaccaggtc agcctgacct gcctggtcaa aggcttctat    1020
cccagcgaca tcgccgtgga gtgggagagc aatgggcagc cggagaacaa ctacaagacc    1080
acgcctcccg tgctggactc cgacggctcc ttcttcctct acagcaagct caccgtggac    1140
aagagcaggt ggcagcaggg gaacgtcttc tcatgctccg tgatgcatga ggctctgcac    1200
aaccactaca cgcagaagag cctctccctg tctccgggta aatga                    1245
```

<210> SEQ ID NO 5
<211> LENGTH: 32
<212> TYPE: DNA
<213> ORGANISM: Artificial Sequence
<220> FEATURE:
<223> OTHER INFORMATION: sDR5 forward primer

<400> SEQUENCE: 5

```
ggaagcttgc caccatggaa caacggggac ag                                    32
```

<210> SEQ ID NO 6
<211> LENGTH: 26
<212> TYPE: DNA
<213> ORGANISM: Artificial Sequence
<220> FEATURE:
<223> OTHER INFORMATION: sDR5 (1-133) reverse primer

<400> SEQUENCE: 6
aagaattctc tggtcgtggt gcaggg                                  26

<210> SEQ ID NO 7
<211> LENGTH: 32
<212> TYPE: DNA
<213> ORGANISM: Artificial Sequence
<220> FEATURE:
<223> OTHER INFORMATION: sDR5 (1-182) reverse primer

<400> SEQUENCE: 7
ggaagcttgc caccttcttt gtggacacat tc                           32

<210> SEQ ID NO 8
<211> LENGTH: 72
<212> TYPE: DNA
<213> ORGANISM: Artificial Sequence
<220> FEATURE:
<223> OTHER INFORMATION: signal peptide forward primer

<400> SEQUENCE: 8
aagcttgggg ccaccatggg atggtcatgt atcatccttt ttctggtagc aactgcaact    60
ggagtacatt ca                                                 72

<210> SEQ ID NO 9
<211> LENGTH: 41
<212> TYPE: DNA
<213> ORGANISM: Artificial Sequence
<220> FEATURE:
<223> OTHER INFORMATION: Fc mutation forward primer

<400> SEQUENCE: 9
gaggtcacat gcgtggtggt ggccgtgagc cacgaagacc c                 41

<210> SEQ ID NO 10
<211> LENGTH: 37
<212> TYPE: DNA
<213> ORGANISM: Artificial Sequence
<220> FEATURE:
<223> OTHER INFORMATION: Fc mutation reverse primer

<400> SEQUENCE: 10
caccaccacg catgtgacct caggggtccg ggagatc                      37

<210> SEQ ID NO 11
<211> LENGTH: 232
<212> TYPE: PRT
<213> ORGANISM: Homo sapiens

<400> SEQUENCE: 11

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Ala Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

```
Tyr Asn Ser Thr Tyr Arg Val Val Ser Val Leu Thr Val Leu His Gln
                85              90              95
Asp Trp Leu Asn Gly Lys Glu Tyr Lys Cys Lys Val Ser Asn Lys Ala
            100             105             110
Leu Pro Ala Pro Ile Glu Lys Thr Ile Ser Lys Ala Lys Gly Gln Pro
        115             120             125
Arg Glu Pro Gln Val Tyr Thr Leu Pro Pro Ser Arg Asp Glu Leu Thr
    130             135             140
Lys Asn Gln Val Ser Leu Thr Cys Leu Val Lys Gly Phe Tyr Pro Ser
145             150             155             160
Asp Ile Ala Val Glu Trp Glu Ser Asn Gly Gln Pro Glu Asn Asn Tyr
            165             170             175
Lys Thr Thr Pro Pro Val Leu Asp Ser Asp Gly Ser Phe Phe Leu Tyr
            180             185             190
Ser Lys Leu Thr Val Asp Lys Ser Arg Trp Gln Gln Gly Asn Val Phe
        195             200             205
Ser Cys Ser Val Met His Glu Ala Leu His Asn His Tyr Thr Gln Lys
        210             215             220
Ser Leu Ser Leu Ser Pro Gly Lys
225             230
```

SDR5-FC FUSION PROTEIN MUTANT AND USE THEREOF

CROSS REFERENCE TO RELATED APPLICATIONS

This application is the U.S. national phase of International Application No. PCT/CN2016/081552 filed May 10, 2016 which designated the U.S. and claims priority to CN Patent Application No. 201510510981.9 filed Aug. 19, 2015, the entire contents of each of which are hereby incorporated by reference.

TECHNICAL FIELD

The present disclosure belongs to the technical field of genetic engineering and protein engineering, and relates to sDR5-Fc fusion protein and use thereof, and more particularly to sDR5-Fc fusion protein and its use in the preparation of medicament for the treatment of myocardial infarction.

BACKGROUND OF RELATED ART

Myocardial ischemia refers to a pathological condition in which the blood perfusion in coronary artery reduces, resulting in the lack of oxygen supply in the heart, the disorders of myocardial energy metabolism, and the bad supporting of the normal work of the heart. Coronary artery stenosis or occlusion is the main and most common cause of myocardial ischemia.

After myocardial ischemia, the process such as thrombolysis, coronary artery bypass surgery or percutaneous coronary angioplasty should be conducted to restore the blood supply to the ischemic myocardium. Reperfusion can save the ischemic myocardium; meanwhile, it could also further aggravate the damage of myocardial cells on the verge of death. This phenomenon of which tissue damage aggravates after the recovery of blood flow, and even irreversible cell death occurs is called ischemia-reperfusion injury.

The mechanism of reperfusion injury involves many cellular and molecular biological events that include ROS production, overloaded intracellular calcium, mitochondrial dysfunction, cell inflammation, autophagy and apoptosis, which cross with each other, form a complex network and eventually lead to the death of myocardial cells. How to develop a targeted drug through detailed research on mechanism to effectively avoid possible reperfusion injury is the focus and difficulty of current research and clinical work. Necrosis was once thought to be the dominant factor in myocardial ischemia-reperfusion injury. While, the role of apoptosis in which is increasingly concerned in recent years. The death receptor pathway activated by the combination of Death receptor 5 (DR5) and tumor necrosis factor-related apoptosis-inducing ligand (TRAIL), can form DISC (death-Inducing signaling complex) by recruiting related proteins, then Caspase-8, Caspase-3 and so on are activated in a cascaded manner, and apoptosis is caused. The full length of DR5 is a type I transmembrane glycoprotein containing 411 amino acids. Soluble death receptor 5 (soluble DR5, sDR5) cannot be expressed on the cell membrane for its lack of transmembrane region and is secreted to extracellular region. sDR5 is lowly expressed in normal human peripheral blood, since it has a complete structure of extracellular domain that can combine with TRAIL ligands, and therefore sDR5 can binds to TRAIL molecules competitively against death receptors on the cell membrane, thereby blocks TRAIL-induced apoptosis.

Studies have shown that: sDR5 could alleviate the liver cell damage caused by hepatitis B virus (HBV) infection by blocking the TRAIL-induced apoptosis, and could also inhibit the apoptosis of brain cells in cerebral ischemia-reperfusion model. At present, there is no report at home and abroad whether sDR5 could improve myocardial ischemia-reperfusion injury by inhibiting apoptosis.

SUMMARY OF THE INVENTION

The object of this disclosure is to provide a sDR5-Fc fusion protein that can be used for the treatment of myocardial ischemia-reperfusion injury. The disclosure has been tested to show that the fusion protein composed of 1-182 N-terminal amino acids of DR5 extracellular domain and human antibody Fc fragment can basically avoid Fc-mediated ADCC effect and can significantly reduce the area of myocardial infarction in rats of myocardial ischemia-reperfusion models.

To achieve the above objective, the disclosure provides the following technical solutions.

The disclosure provides a fusion protein, and the fusion protein consists of a sDR5 fragment and the Fc fragment of human antibody. The sDR5 fragment is the entire amino acid sequence of the DR5 extracellular region or the partial amino acid sequence thereof as long as it retains the activity of binding to the TRAIL ligand. The fusion protein is named as sDR5-Fc.

Preferably, an amino acid sequence of the sDR5 fragment is any one of the following groups:

(1) the amino acid sequence shown in SEQ ID NO. 1;

(2) an amino acid sequence obtained by substitution and/or deletion and/or addition of one or several amino acids in the amino acid sequence shown in SEQ ID NO. 1 and having the same or similar function compared to the amino acid sequence shown in SEQ ID NO. 1.

(3) an amino acid sequence having at least 99% homology and having the same function as the amino acid sequence defined by (1) or (2).

More preferably, the amino acid sequence of the sDR5 fragment is shown in SEQ ID NO. 1.

Preferably, the number of one or several amino acids substituted and/or deleted and/or the added in the amino acid sequence shown in SEQ ID NO. 1 does not exceed 10.

The "Fc fragment of human antibody" in the disclosure means a "human immunoglobulin heavy chain constant region", which could be derived from an antibody belonging to any immunoglobulin class called as Ig A, Ig D, Ig E, Ig G and Ig M. In addition, it is contemplated that the immunoglobulin heavy chain constant region could be derived from any one of the Ig G antibody subclasses known in the art as Ig G1, Ig G2, Ig G3 and Ig G4.

Preferably, the Fc fragment of human antibody of the disclosure is derived from human antibody Ig G1.

Preferably, the amino acid sequence of the Fc fragment of human antibody of the disclosure is any one of the following groups:

(1) the amino acid sequence shown in SEQ ID NO. 2;

(2) an amino acid sequence obtained by substitution and/or deletion and/or addition of one or several amino acids in the amino acid sequence shown in SEQ ID NO. 2 and having the same or similar function compared to the amino acid sequence shown in SEQ ID NO. 2;

(3) an amino acid sequence having at least 98% homology and having the same function as the amino acid sequence defined in (1) or (2).

More preferably, the amino acid sequence of the Fc fragment of human antibody is as shown in SEQ ID NO. 2.

The amino acid sequence of the fusion protein sDR5-Fc of the disclosure is any one of the following groups:

(1) the amino acid sequence as shown in SEQ ID NO. 3;

(2) an amino acid sequence obtained by substitution and/or deletion and/or addition of one or several amino acids in the amino acid sequence shown in SEQ ID NO. 3 and having the same or similar function compared to the amino acid sequence shown in SEQ ID NO. 3;

(3) an amino acid sequence having at least 98% homology and having the same function as the amino acid sequence defined in (1) or (2).

Preferably, the amino acid sequence of the fusion protein sDR5-Fc of the disclosure is shown in SEQ ID NO. 3.

In the sDR5-Fc sequence which is different from wild-type sDR5-Fc sequence due to one or more conserved amino acid substitutions or one or more non-conservative amino acid substitutions, deletions, or insertions, the substitutions, deletions or insertions do not abrogate the biological activity of the wild-type sequence. Conserved substitutions typically include an amino acid substitution with another amino acid having similar characteristics, for example, substitutions among the following groups: valine, glycine; glycine, alanine; valine, isoleucine, leucine; aspartic acid, glutamic acid; asparagine, glutamine; serine, threonine; lysine, arginine; and phenylalanine, tyrosine. Other conserved amino acid substitutions are known in the art and are included herein. Non-conservative substitutions, for example, basic amino acids are replaced by hydrophobic amino acids, are also well known in the art.

The modifications of the fusion protein sDR5-Fc of the disclosure for increasing protein or peptide stability are also included within the scope of the disclosure; such modifications include the presence of, for example, one or more non-peptide bonds in a protein or peptide sequence (substituting peptide bonds); such modifications also include amino acids comprising D-amino acids or non-naturally existed or synthetic amino acids, such as beta or gamma amino acids.

The disclosure provides a DNA molecule encoding the fusion protein sDR5-Fc as described above.

Furthermore, the nucleotide sequence of the DNA molecule is any one of the following groups:

(1) the nucleotide sequence as shown in SEQ ID NO 4 or a degenerate sequence thereof;

(2) a nucleotide sequence obtained by substitution and/or deletion and/or addition of one or several nucleotides in the nucleotide sequence shown in SEQ ID NO: 4; the nucleotide sequence encodes the same or similar protein compared to the nucleotide sequence shown in SEQ ID NO. 4 or its degenerate sequence;

(3) a nucleotide sequence that hybridizes with the nucleotide sequence defined by (1) under stringent conditions and has the same function as that of the nucleotide sequence defined by (1);

(4) a nucleotide sequence having at least 98% homology and having the same function as that of the nucleotide sequence defined by (1).

Preferably, the nucleotide sequence of the DNA molecule encoding the fusion protein sDR5-Fc as described above is shown in SEQ ID NO. 4.

The "stringent conditions" described in the disclosure could be specific for hybridization at 65° C. with the nucleotide sequence shown in SEQ ID NO. 4 in 6×SSC, 0.5% SDS solution, the membranes are then washed once respectively by 2×SSC, 0.1% SDS and 1×SSC, 0.1% SDS. A nucleotide sequence that hybridizes with the nucleotide sequence defined in SEQ ID NO. 4 under stringent conditions and has the same function has at least about 40%-50% homologous, about 60%, 65% or 70% homologous, or even at least 98% or more homologous to the sequence shown in SEQ ID NO. 4. The range of sequence identity is at least about 40%-50%, about 60%, 65%, or 70% homologous, even at least about 75%, 80%, 85%, 90%, 91%, 92%, 93%, 94%, 95%, 96%, 97%, 98%, 99% or greater sequence homology.

The disclosure provides a recombinant vector comprising the DNA molecule encoding the fusion protein sDR5-Fc as described above.

As used herein, the term "vector" is to be understood as encompassing any nucleic acid that can be incorporated into a host cell and recombined with the host cell genome and integrated into the host cell genome, or any nucleic acid of which nucleotide sequence that autonomously replicates as free radicals. Such vectors include linear nucleic acids, plasmids, phagemid, cosmid, RNA vectors, viral vectors, and so on.

The vectors applicable for the disclosure include, but not limited to, expression vectors, cloning vectors, for example, the vectors applicable for prokaryotic cells (e.g., bacteria such as *Escherichia coli*), lower eukaryotic cells (e.g., yeast), insect cells, plant cells, and mammalian cells. In short, any plasmid and vector can be used as long as it can replicate and be stable in the host. In the expression vector, in addition to the origin of replication, the marker gene and other translation control elements may also be included.

Virus vectors that can be used in the disclosure include, but not limited to, adenoviral vectors, adeno-associated viral vectors, retroviral vectors, herpes simplex virus-based vectors, and lentiviral vectors.

Preferably, the vector of the disclosure uses the eukaryotic expression vector pGS-Fc.

The disclosure also provides a host cell comprising the recombinant vector as described above.

Furthermore, the host cell may be prokaryotic cells, such as bacterial cells; or lower eukaryotic cells, such as yeast cells; or higher eukaryotic cells, such as mammalian cells. Representative examples are: *Escherichia coli, Streptomyces*; bacterial cells of *Salmonella typhimurium*: fungal cells such as yeast; plant cells; insect cells of *Drosophila* S2 or Sf9; animal cells of CHO, COS, 293 cells or Bowes melanoma cells and so on.

The disclosure also provides a process for the preparation of the fusion protein sDR5-Fc as described above:

(1) Constructing recombinant vector comprising sDR5-Fc fragments;

(2) Introducing the recombinant vector into the host cell to express the sDR5-Fc fusion protein;

(3) Isolating and purifying sDR5-Fc fusion protein.

Furthermore, there are more than one type of expression system capable of expressing these fusion proteins, which could be eukaryotic cells or prokaryotic cells, including (but not limited to) mammalian cells, bacteria, yeasts, insect cells and the like. Since the amino acid sequence of the optimized fusion protein of the disclosure contains glycosylated amino acids, the mammalian cell is a preferred system for expressing the protein. There are more than one type of mammalian cells that can be used for expressing proteins on a large-scale, such as CHO cells, 293 cells, NS0 cells, COS cells, BHK cells and the like, and many other cells can also be used for expressing protein and are therefore included in the cells that can be used in the disclosure. Other expression systems other than mammalian cells, such as bacteria, yeasts, insect cells, etc., could also be used to express the optimized fusion proteins of the disclosure, and are also included in the list of host cells that can be used in the disclosure. The protein yields of these expression systems are higher than that of mammalian cells, but the expressed protein lacks glycosylation or the sugar chain structure formed is different from that of mammalian cells.

Recombinant plasmids containing the above fusion protein gene can be transfected into host cells, and there are a variety of methods for transfection of cells, including (but not limited to) electroporation, liposome transfection and calcium phosphate transfection etc.

Since these fusion proteins contain immunoglobulin Fc, the expressed fusion protein can be purified by protein A affinity chromatography. In addition, the fusion protein of the disclosure can be further purified in combination with other protein purification methods such as ion exchange chromatography and the like.

The disclosure also provides a use for preparation of a medicament for the treatment of myocardial infarction of the fusion protein sDR5-Fc as described above, the DNA molecule encoding a fusion protein sDR5-Fc as described above, the recombinant vector as described above, or the host cell comprising the recombinant vector as described above.

The disclosure also provides a pharmaceutical composition comprising the fusion protein sDR5-Fc as described above, the DNA molecule encoding the fusion protein sDR5-Fc as described above, the recombinant vector as described above, or the host cell comprising the recombinant vector as described above.

Furthermore, the pharmaceutical compositions of the disclosure also include a pharmaceutically acceptable carrier, including but not limited to any adjuvant, excipient, glidant, sweetening agent, diluents, preservative, dye/colorant, flavor enhancer, surfactant, wetting agent, dispersant, suspending agent, stabilizer, isotonic agent, solvent or emulsifier and the like that have no side effects on the composition of the pharmaceutical composition which has been approved by the US Food and Drug Administration and can be used for humans or animals.

The pharmaceutical compositions of the disclosure could be administered in a variety of means, for example, oral, sublingual, mouth, parenteral, nasal, local, transrectal, transdermal, transmucosal administration and the like.

Depending on administration form of the pharmaceutical composition, the pharmaceutical compositions may be prepared into corresponding dosage forms, including but not limited to, tablets, solutions, granules, patches, pastes, capsules, aerosols, and suppositories.

The compositions of the disclosure may be administered, for example, in a form suitable for immediate release or sustained release. Immediate release or sustained release can be achieved by using a suitable pharmaceutical composition, or in particular in a sustained release case, by means such as a subcutaneous implant or an osmotic pump.

The subject to be treated is a patient suffering myocardial ischemic injury, including but not limited to mammals such as humans, dogs, cats, and the like.

It should be appreciated that the specific dosage levels and dosage frequencies for any particular subject may vary and will depend on a variety of factors including the activity of the pharmaceutical composition used; the metabolic stability and duration of action of the pharmaceutical composition; age, weight, general health status, sex and diet of the subject; pattern and time of administration; rate of excretion and clearance; drug combination; and severity of a particular condition.

The pharmaceutical compositions of the disclosure may be used alone or in combination with other suitable therapeutic agents useful for the treatment of myocardial ischemic injury, or with other surgery methods of treatment for myocardial ischemic injury.

The "treatment" as described in the disclosure includes thorough cure of the disease, as well as a remission of the disease.

As used herein, the term "gene expression"; or "expression"; should be interpreted as the transcription of DNA sequences, translation of mRNA transcripts, and secretion of Fc fusion protein products.

The "mutant"; and "wild type"; as used in the context of the disclosure are directed to the sequence of Fc fragments. The mutant site of the "fusion protein mutant" is on the Fc fragment.

The advantages and beneficial effects of the disclosure are as follows:

(1) The sDR5 (1-182)-Fc fusion protein mutant was constructed for the first time, and the use of the fusion protein reduces the ADCC effect due to the mutation of the Fc fragment.

(2) The sDR5 (1-182) fragment selected in the sDR5 (1-182)-Fc fusion protein mutant of the disclosure has the following advantages over other fragments of the DR5 extracellular region: high expression, easily obtained, strong binding capability with TRAIL ligand, weak ADCC effect, and stronger effects of inhibiting myocardial injury.

DETAILED DESCRIPTION OF THE EMBODIMENT

The disclosure will now be further described with reference to specific embodiments. It is to be understood that these examples are merely illustrative of the disclosure and are not intended to limit the scope of the disclosure. The experimental methods not specified in the following examples are generally carried out according to conventional conditions such as those described in Sambrook et al., Molecular Cloning: Laboratory Guide (New York: Cold Spring Harbor Laboratory Press, 1989), or in accordance with the conditions recommended by the manufacturer. Unless otherwise stated, the percentages and parts are calculated by weight. Unless otherwise defined, all professional and scientific terms used herein are of the same meaning as those skilled in the art familiar with. In addition, any method and material similar to or equivalent to the contents described may be applied to the disclosure. The preferred embodiments and materials described herein are only for exemplary purposes.

Example 1 Expression, Purification and Identification of sDR5-Fc Fusion Protein 1. sDR5-Fc Eukaryotic Expression Plasmid was Constructed 1.1 sDR5-Fc Fusion Protein Wild-Type Expression Plasmid was Constructed 1) *Pichia pastoris* GS115 strain containing pGAPZαA-sDR5 (see: Song K, Chen Y, Goke R, et al. Tumor necrosis factor-related apoptosis-inducing ligand (TRAIL) is an inhibitor of autoimmune inflammation and cell cycle progression. J Exp Med, 2000; 191(7):1095-1104) was used as PCR templates to amplify encoding gene fragments of sDR5 (1-133), sDR5 (1-182), the new signal peptide (sp)-sDR5 (56-182), and the new signal peptide (sp)-sDR5 (56-133).

The amplification primers were designed as follows:

```
sDR5 (1-133):
Forward primer:
                                          (SEQ ID NO. 5)
5'-ggaagcttgccaccATGGAACAACGGGGACAG-3';

Reverse primer:
                                          (SEQ ID NO. 6)
5'-aagaattcTCTGGTCGTGGTGCAGGG-3', sDR5 (1-182):
Forward primer:
                                          (SEQ ID NO. 5)
5'-ggaagcttgccaccATGGAACAACGGGGACAG-3';

Reverse primer:
                                          (SEQ ID NO. 7)
5'-ggaagcttgccaccTTCTTTGTGGACACATTC-3', New signal peptide (sp)-sDR5 (56-182):
Forward primer:
                                          (SEQ ID NO. 8)
5'-
AAGCTTGGGGCCACCATGGGATGGTCATGTATCATCCTTTTTCTGGTAG

CAACTGCAACTGGAGTACATTCA-3';
```

```
Reverse primer:
                                          (SEQ ID NO. 7)
5'-ggaagcttgccaccTTCTTTGTGGACACATTC-3', New signal peptide (sp)-sDR5 (56-133):
Forward primer:
                                          (SEQ ID NO. 8)
5'-
AAGCTTGGGGCCACCATGGGATGGTCATGTATCATCCTTTTTCTGGTAG

CAACTGCAACTGGAGTACATTCA-3';

Reverse primer:
                                          (SEQ ID NO. 6)
5'-aagaattcTCTGGTCGTGGTGCAGGG-3'.
```

2) The gene fragment of step (1) was cloned into the eukaryotic expression vector pGS-Fc carrying human IgG Fc fragment. The pGS-Fc multiple cloning site was inserted through the double enzyme digestion with Hind III and EcoR I.

1.2 sDR5-Fc Fusion Protein Mutant Expression Plasmid was Constructed by Using Point Mutagenesis Kit The process was operated in accordance with the kit instructions (Toyobo, SMK-101), the mutant primers of Fc fragment were:

```
Forward primer:
                                          (SEQ ID NO. 9)
5'-gaggtcacatgcgtggtggtggccgtgagccacgaagaccc-3';

Reverse primer:
                                          (SEQ ID NO. 10)
5'-caccaccacgcatgtgacctcaggggtccgggagatc-3',
```

The amino acid sequence after the mutation of the wild-type Fc fragment was as follows:

epkscdktht cppcpapell ggpsvflfpp kpkdtlmisr tpevtcvvva vshedpevkf nwyvdgvevh naktkpreeq ynstyrvvsv ltvlhqdwln gkeykckvsn kalpapiektiskakgqpre pqvytlppsr deltknqvsl tclvkgfyps diavewesng qpennykttp pvldsdgsff lyskltvdks rwqqgnvfsc svmhealhnh ytqkslslsp gk (SEQ ID NO. 11).

The site of 265 on Fc fragment mutant is Ala, the site of 265 on Fc fragment of wild type is Asp.

2. The recombinant expression plasmid was amplified and the recombinant expression plasmid constructed in step 1 was introduced into prokaryotic host cell and amplified.

3. The high purity plasmid (OMEGA Plasmid Midi Kit) was extracted and its concentration was adjusted to 500 ng/μl, the plasmid was transiently transfected into 293T cells, the supernatant and the cells were collected after 48 hrs, the supernatant and the cell lysate were adsorbed by using Protein A/G particles, and the expression of the fusion protein was detected by using Western blot.

4. 5 Fusion Protein Expression Plasmids were Transfected into CHO/K1 Cells

The cells were conditioned to the best and transiently transferred (300 v, interval 0.125 s, duration 0.1 ms, shock three times), after 24 hours, the supernatant was collected and purified by affinity chromatography column to obtain the human sDR5-Fc fusion protein. The fusion protein was determined by Coomassie brilliant blue staining after SDS-PAGE, and the fusion protein yield of the disclosure could achieve 30 mg/L.

5. Results

Figure 1:
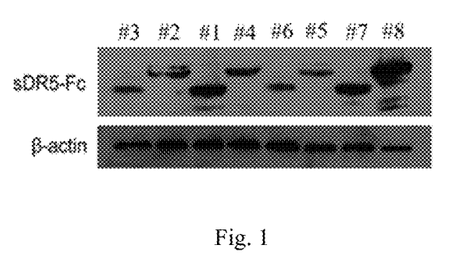
FIG. 1 shows the expression of eight purified human sDR5-Fc fusion proteins verified by Western Blot, where #1: new signal peptide (sp)-sDR5 (56-133)-Fc mutant; #2: sDR5 (1-182)-Fc mutant; #3: sDR5 (1-133)-Fc mutant; #4: new signal peptide (sp)-sDR5 (56-182)-Fc mutant; #5: sDR5 (1-182)-Fc wild type; #6: sDR5 (1-133)-Fc wild type; #7: new signal peptide (sp)-sDR5 (56-133)-Fc wild type; #8: new signal peptide (sp)-sDR5 (56-182)-Fc wild type.

As shown in FIG. 1, the constructed eight sDR5-Fc fusion proteins could be expressed in 293T cells. Wherein, #1: new signal peptide (sp)-sDR5 (56-133)-Fc mutant; #2: sDR5

Figure 2:
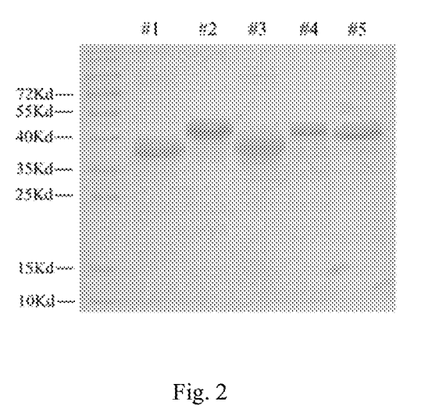
FIG. 2 shows the expression of human sDR5-Fc in CHO-K1 supernatant identified by SDS-PAGE Coomassie brilliant blue staining, wherein, #1: new signal peptide (sp)-sDR5 (56-133)-Fc mutant; #2: sDR5 (1-182)-Fc mutant; #3: sDR5 (1-133)-Fc mutant; #4: new signal peptide (sp)-sDR5 (56-182)-Fc mutant; #5: SDR5 (1-182)-Fc wild type.

(1-182)-Fc mutant; #3: sDR5 (1-133)-Fc mutant; #4: new signal peptide (sp)-sDR5 (56-182)-Fc mutant; #5: sDR5 (1-182)-Fc wild type; #6: sDR5 (1-133)-Fc wild type; #7: New signal peptide (sp)-sDR5 (56-133)-Fc wild type; #8: new signal peptide (sp)-sDR5 (56-182)-Fc wild type;

As shown in FIG. 2, the selected five sDR5-Fc fusion proteins could be expressed in the supernatant of CHO/K1 cells. #1: new signal peptide (sp)-sDR5 (56-133)-Fc mutant; #2: sDR5 (1-182)-Fc mutant; #3: sDR5 (1-133)-Fc mutant; #4: new signal peptide (sp)-sDR5 (56-182)-Fc mutant; #5: sDR5 (1-182)-Fc;

Example 2 Determination of Affinity Between Human sDR5-Fc and TRAIL

The affinity between human sDR5-Fc and TRAIL was determined by using an ELISA method.

1. Steps:

(1) Coating

The coating antigen TRAIL was diluted with CBS by doubling dilution from 2 μg/mL (2, 1, 0.5 μg/mL), 100 μL/well, coated at 4° C. overnight;

(2) Washing

The solution in plate was thrown out, pat dried, and the plate was washed with washing liquid for 3 times, 2 min per time;

(3) Blocking

The washing liquid in plate was thrown out, and then the plate was pat dried on absorbent paper out of fiber, and then 250 μL of blocking solution was added per well, and then the plate reacted at 37° C. in the incubator for 1.5 h; dried standby;

(4) Adding Samples

The sDR5-Fc was diluted from 1:500 to 1:40000 and added to the coating wells with different dilutions, 100 μL per well and the plate was reacted at 37° C. in the incubator for 1 h. After sufficient washing, the secondary antibody HRP-goat anti-human IgG diluted with enzyme diluent in 1:5000 was added, 100 μL per well, the plate was reacted at 37° C. in the incubator for 1 h;

(5) Color Development

The enzyme plate was taken out, the second step was repeated to wash, and then 50 μL of color reagent A and B were added respectively into each hole, the plate reacted at room temperature away from light for 15 min;

(6) Termination and Measurement

The stop solution was added, 50 μL per well to terminate the color reaction, and then the microplate reader was used to determine the $OD_{450}$ value of each hole.

(7) The Results of Interpretation

The value of $OD_{450}$ greater than or equal to 2.1 times that of the negative hole (ie, P/N≥2.1) was determined to be positive.

Figure 3:
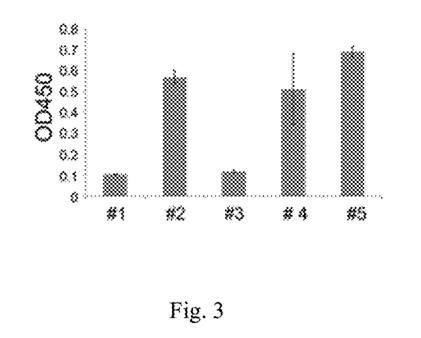
FIG. 3 shows the affinity between human sDR5-Fc fusion protein and TRAIL measured by ELISA, wherein, #1: new signal peptide (sp)-sDR5 (56-133)-Fc mutant; #2: sDR5 (1-182)-Fc mutant; #3: sDR5 (1-133)-Fc mutant; #4: new signal peptide (sp)-sDR5 (56-182)-Fc mutant; #5: sDR5 (1-182)-Fc wild type.

2. Results:

As the results shown in FIG. 3, #2: sDR5 (1-182)-Fc mutant, #4: new signal peptide (sp)-sDR5 (56-182)-Fc mutant, and #5: sDR5 (1-182)-Fc wild type has higher affinity with TRAIL.

Example 3 the Effect of Human sDR5-Fc Fusion Protein on TRAIL-Induced Apoptosis

1. Steps: Jurkat cells were suspension cultured in 100 mm cell culture dish, the culture medium was 1640 medium containing 10% serum, 3-4 generations of cells in good growing state were collected, centrifuged for 10 min at 500 g and counted, the cells were paved in 96-well plate, and each treatment factor was for 4 holes. Blank control wells, TRAIL alone wells, 5 selected sDR5-Fc blocking groups, and hIgG-Fc isotype control group. The treatment of TRAIL blocking group was to premix and incubate TRAIL and blocking protein for 30 min. The working concentration for TRAIL is 250 ng/ml, and the working concentration for blocking protein is 5 μg/ml.

Figure 4:
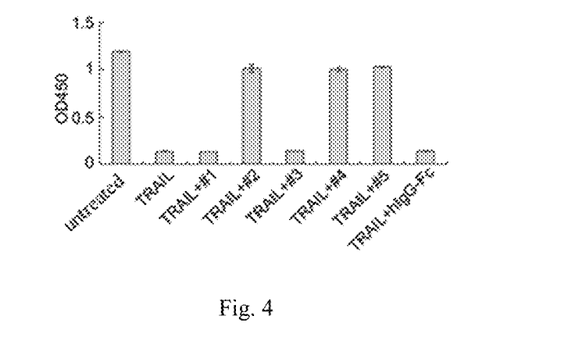
FIG. 4 shows the effect of human sDR5-Fc fusion protein on TRAIL-induced apoptosis; wherein, #1: new signal peptide (sp)-sDR5 (56-133)-Fc mutant; #2: sDR5 (1-182)-Fc mutant; #3: sDR5 (1-133)-Fc mutant; #4: new signal peptide (sp)-sDR5 (56-182)-Fc mutant; #5: sDR5 (1-182)-Fc wild type.

2. Results:

As the results shown in FIG. 4, the blocking effect of #2: sDR5 (1-182)-Fc mutant, #4: new signal peptide (sp)-sDR5 (56-182)-Fc mutant, and #5: sDR5 (1-182)-Fc wild type is good, which demonstrates that sDR5-Fc fusion protein could block the apoptosis of the TRAIL-induced Jurkat cell well.

Example 4 Determination of Affinity Between sDR5 (1-182)-Fc Mutant and Fc Receptor and Affinity Between sDR5 (1-182)-Fc Wild Type and Fc Receptor Considering the protein expression, the affinity with TRAIL, and the ability to block TRAIL-induced apoptosis of several sDR5-Fc fusion proteins, sDR5 (1-182)-Fc mutant and sDR5 (1-182)-Fc wild Type were selected to conduct the following experiments.

1. Steps: Fc receptor coated plate was used to conduct the measurement of ELISA, and the operating steps were the same as that in Example 2.

2. Results

Figure 5:
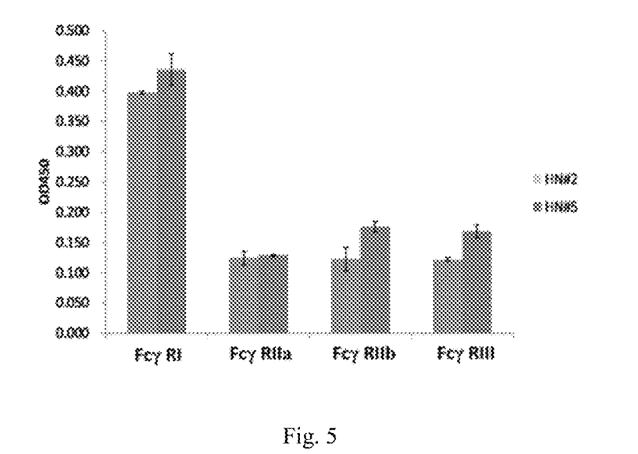
FIG. 5 shows the affinity between sDR5 (1-182)-Fc mutant and Fc receptors and the affinity between sDR5 (1-182)-Fc wild type and Fc receptors measured by ELISA; wherein, #2: sDR5 (1-182)-Fc mutant; #5: sDR5 (1-182)-Fc wild type.

As the results shown in FIG. 5, compared to the #5: sDR5 (1-182)-Fc wild type, the affinity was lower between #2: sDR5 (1-182)-Fc mutant and three Fc receptors FcgammaRl, FcgammaRllb, and FcgammaRlll.

Example 5 Detection of ADCC Effect of sDR5 (1-182)-Fc Mutants

1. The Acquisition of Lymphocyte 1) 10 ml of heparin anticoagulant was taken from the peripheral blood of two healthy people, centrifuged at 250 g for 10 minutes at 18-22° C., the plasma was discarded, whole blood and tissue dilution were supplemented, the supplemented amount thereof is of 1.5-2 times of the discarded plasma volume, blended standby.

2) An appropriate centrifuge tube was taken and the separating fluid (equal to the volume of the diluted blood sample) was added, and placed at 18-22° C.

3) The diluted blood sample was carefully spread on the surface of separating fluid and centrifuged at 400 g for 20 minutes at 18-22° C.

4) After centrifugation, the supernatant fraction of the upper layer above 0.5 cm from the separating fluid was carefully sucked out with a pipette, and discarded.

5) The separating fluid layer and the lymphocyte layer were carefully inhaled into another new centrifuge tube with a pipette.

6) The centrifuge tube obtained in step 5 was added with 10 ml cell washing solution, and mixed.

7) Centrifuged at 250 g for 10 minutes.

8) The supernatant was discarded.

9) The cells were resuspended in a 5 ml cell washing solution with a pipette.

10) Centrifuged at 250 g for 10 min.

11) The supernatant was discarded. Steps 8, 9 and 10 were repeated, then the cells were resuspended with 1 ml of 1640 medium containing 10% FBS and counted.

2. ADCC Detection

1) A 96-well plate was taken and each hole was added with 50 µl of target cells in logarithmic phase (H9C2 and Jurkat) (1×10⁵/ml), and then added with 50 µl of recombinant protein sDR5 (1-182)-Fc mutant (200 µg/ml), cultivated for 2 h at 37° C. with 5% $CO_2$.

2) The corresponding wells were added with 100 µl of cell suspension in different concentrations obtained from Step 1, the number of cells were 2×10⁵/well (target cells:lymphocytes=1:40) and 5×10⁵/well (target cells:lymphocytes=1:100) respectively. At the same time, empty culture medium, individual lymphocytes and individual target cells were used as 3 negative controls, and the positive control of target cell lysate was also set.

3) The plate was cultivated for 48 h at 37° C. with 5% $CO_2$.

4) Following the instructions of the LDH kit (Roche, 11644793001), the appropriate reagent was added, then the absorbance at 490 nm was measured.

Figure 6:
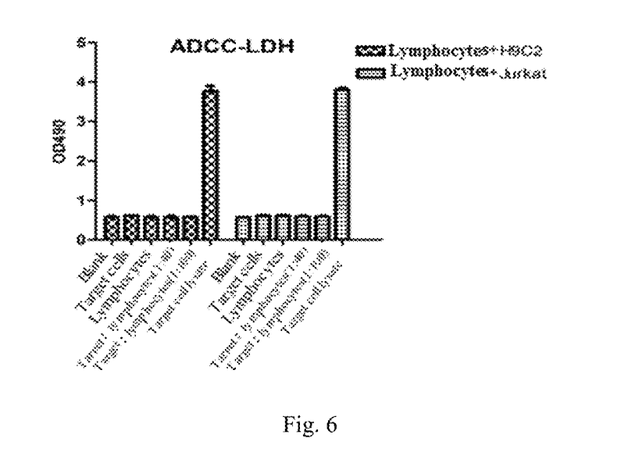
FIG. 6 shows the ADCC effect of the sDR5 (1-182)-Fc mutant measured by LDH assay.

3. Results:

As the results shown in FIG. 6, the sDR5 (1-182)-Fc mutant has almost no ADCC effect.

Example 6 Protective Effects of sDR5 (1-182)-Fc Mutant on Myocardial Cells in Rats with Myocardial Infarction 1. Preparation for the Rat Model of Three Hours of Reperfusion after 1 h of the Myocardial Ischemia The ischemia-reperfusion model was established by ligating/releasing anterior descending coronary artery on rats: the clean male wistar rats (200-250 g in body weight), was anesthetized by intraperitoneal injection with 10% chloral hydrate (3-4 ml/kg), trachea was intubated and the intercostal space was opened before access to the ventilator, the parameters were adjusted to the breathing ratio of 1:2, breathing frequency of 90-120 times/min, and tidal volume of 2-4 ml; sternal left margin 3-4 intercostal were transected, the pericardium was cut, the heart was exposed, the left coronary vein at the junction of pulmonary artery cones and left auricle was set as the mark, and the ligation was made by threading bypass the left anterior descending branch in the left lower ear of the median about 0.1 cm, while the sham operation group was set as a control (only threaded and does not ligated). Penicillin 400,000 U per rat only was regularly injected after the surgery.

The rats of coronary artery ligation were randomly divided into PBS group and sDR5 (1-182)-Fc mutant group, each group was subdivided into three groups according to different doses, six rats in each subgroup and the experiment was repeated for three times, the specific experimental methods and results were described as follows:

After 1 h of the ligation of coronary artery, human sDR5-Fc group was injected with human sDR5 (1-182)-Fc mutant through rat tail vein; PBS group was injected with the corresponding dose of sterile PBS through tail vein.

2. TTC-Evans Blue Staining in Rat Myocardial Tissue

Rat was anesthetized with chloral hydrate, the chest was opened and the aorta was ligated, after re-ligation of the left anterior descending coronary artery, 5 ml 1% Evans Blue was injected from the left ventricle at a moderate speed; and then the left ventricle was quickly cut, Rinsed three times in saline, freezed at −20° C. for at least 1 h. The tissue was removed from the refrigerator and quickly cut into 1-2 mm thick sections on a tin foil and placed in a 12-well plate containing TTC dye solution, incubated at 37° C. for 15 min, and then the redundant dye on tissue surface was washed away by using the tissue washing applied solution (TTC dye solution kit, Nanjing built Technology Co., Ltd.), observed and photographed, wherein the white was for the infarct area, blue was for normal myocardium, red and white was for risk areas.

Compared with the sham operation group, the myocardial area of the rats injected with PBS showed a large area of gray area (ie, infarct area), while infarct area of the sDR5-Fc injected narrowed, and calculation method of myocardial infarct area were: myocardial weight of the infarcted area/myocardial weight of risk area×100%; The calculation method of reduction rate of myocardial infarct area: (infarct area of control group−infarct area of treatment group)/infarct area of control group×100%. The infarct area was expressed as IS, the risk area was expressed as AAR, the left ventricle was expressed as LV, and the myocardial infarct area was expressed as the ratio of IS/AAR, and the myocardial ischemia area was expressed as AAR/LV.

3. Results

Figure 7:
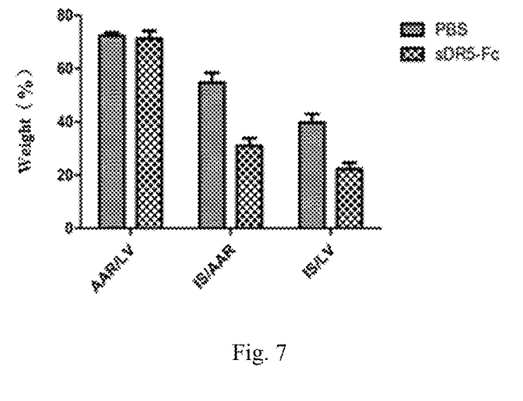
FIG. 7 shows the protective effect of human sDR5 (1-182)-Fc mutant on cardiomyocytes.

As the results shown in FIG. 7, in the rat model of three hours of reperfusion after 1 h of the myocardial ischemia, 15 mg/kg of sDR5 (1-182)-Fc mutant of single injection into the tail vein at the first 5 min of reperfusion can significantly reduce the myocardial infarct area by more than 40%, compared with the control group.

The foregoing descriptions is a further detailed description of the disclosure in connection with specific preferred embodiments, and it is not to be determined that the specific implementation of the disclosure is limited to these illustrations. It will be apparent to those skilled in the art to which this disclosure pertains that various modifications or substitutions may be made without departing from the spirit of the disclosure, and should be considered as falling within the scope of the disclosure.

What is claimed is:

1. A fusion protein consisting of a sDR5 fragment and a Fc fragment of a human antibody; wherein the amino acid sequence of the sDR5 fragment is
   the amino acid sequence shown in SEQ ID NUMBER 1; and
   wherein the amino acid sequence of the Fc fragment of human antibody is any one of the following group:
   (1) the amino acid sequence shown in SEQ ID NUMBER 2; and
   (2) the amino acid sequence obtained by replacing Asp at position 50 with Ala in the amino acid sequence shown in SEQ ID NUMBER 2.

2. A pharmaceutical composition, wherein the pharmaceutical composition comprises the fusion protein as claimed in claim 1 and a pharmaceutically acceptable carrier.

3. A DNA molecule encoding the fusion protein as claimed in claim 1.

4. The DNA molecule as claimed in claim 3, wherein the nucleotide sequence of the DNA molecule is any one of the following group:
   (1) the nucleotide sequence as shown in SEQ ID NUMBER 4; and
   (2) the nucleotide sequence obtained by replacing "a" at position 705 with "c", or replacing "c" at position 706 with "a" while replacing "a" at position 705 with "c" in the nucleotide sequence as shown in SEQ ID NUMBER 4.

5. A recombinant vector comprising the DNA molecule as claimed in claim 3.

6. The recombinant vector as claimed in claim 5, wherein the recombinant vector is a non-viral vector.

7. An isolated host cell comprising the recombinant vector as claimed in claim 5.

8. A method for treating myocardial infarction in a subject in need thereof comprising administering a therapeutically effective amount of the fusion protein as claimed in claim 1.

* * * * *